US 6,719,719 B2

(12) United States Patent
Carmel et al.

(10) Patent No.: US 6,719,719 B2
(45) Date of Patent: Apr. 13, 2004

(54) SPIKE FOR LIQUID TRANSFER DEVICE, LIQUID TRANSFER DEVICE INCLUDING SPIKE, AND METHOD OF TRANSFERRING LIQUIDS USING THE SAME

(75) Inventors: Ehoud Carmel, Kirat Ono (IL); Gilad Lavi, Rishon Letzion (IL); Gil Yigal, Gan-Yavne (IL); Izrail Tsals, Sudbury, MA (US)

(73) Assignee: Elan Pharma International Limited (IE)

( * ) Notice: Subject to any disclaimer, the term of this patent is extended or adjusted under 35 U.S.C. 154(b) by 50 days.

(21) Appl. No.: 09/863,539

(22) Filed: May 23, 2001

(65) Prior Publication Data

US 2002/0004643 A1 Jan. 10, 2002

Related U.S. Application Data

(63) Continuation-in-part of application No. 09/439,963, filed on Nov. 12, 1999, now Pat. No. 6,478,771.
(60) Provisional application No. 60/108,382, filed on Nov. 13, 1998, and provisional application No. 60/131,644, filed on Apr. 29, 1999.

(51) Int. Cl.[7] .......................... A61M 37/00; A61M 5/00; A61B 19/00
(52) U.S. Cl. .......................... 604/82; 604/92; 604/191; 604/411; 604/416
(58) Field of Search .............................. 604/82, 83, 84, 604/85, 86, 87, 88, 91, 92, 183, 191, 200–201, 244, 411, 412, 413, 414, 416; 128/912

(56) References Cited

U.S. PATENT DOCUMENTS 3,885,607 A * 5/1975 Peltier .................. 141/329
3,923,059 A 12/1975 Ogle (List continued on next page.)

FOREIGN PATENT DOCUMENTS

| WO | WO 96/26702 | * 9/1996 | ............ A61J/1/20 |
| WO | WO 97/46203 | 12/1997 | |
| WO | WO 01/72354 A2 | 10/2001 | |

OTHER PUBLICATIONS

International Search Report dated Nov. 8, 2002, for International Application No. PCT/US02/15481.

Primary Examiner—Biran L. Casler
Assistant Examiner—Catherine S. Williams
(74) Attorney, Agent, or Firm—Caesar, Rivise, Bernstein, Cohen & Pokotilow, Ltd.

(57) ABSTRACT

A spike for facilitating the introduction of liquid under pressure into a container containing a substance is provided which includes an elongate spike shaft having a spike side wall, a longitudinal axis, a distal end and a proximally located end portion, where the distal end has a sharp, pointed tip. An introduction channel is located within the spike shaft for receiving liquid into the container where a portion of the introduction channel is angled to cause liquid to travel out of the introduction channel in a direction non-parallel to the longitudinal axis of the spike shaft. An extraction channel may be included within the spike shaft for removing liquid from the container, where the extraction channel extends through the elongate spike shaft towards the proximally located end portion.

39 Claims, 4 Drawing Sheets

U.S. PATENT DOCUMENTS

| | | | |
|---|---|---|---|
| 4,534,758 A | * | 8/1985 | Akers et al. .................. 604/85 |
| 4,573,967 A | * | 3/1986 | Hargrove et al. ........... 604/411 |
| 4,573,993 A | * | 3/1986 | Hoag et al. ................. 604/411 |
| 4,624,667 A | | 11/1986 | Rutnarak |
| 4,735,608 A | * | 4/1988 | Sardam ...................... 604/411 |
| 4,834,744 A | * | 5/1989 | Ritson ........................ 604/411 |
| 5,221,272 A | | 6/1993 | Proni |
| 5,397,303 A | * | 3/1995 | Sancoff et al. .............. 604/413 |
| 5,454,786 A | | 10/1995 | Harris |
| 5,533,647 A | * | 7/1996 | Long-Hsiung ............... 222/83 |
| 5,791,466 A | | 8/1998 | Tsals |
| 5,989,237 A | | 11/1999 | Fowles et al. |
| 6,019,750 A | | 2/2000 | Fowles et al. |
| 6,063,068 A | | 5/2000 | Fowles et al. |
| 6,071,270 A | | 6/2000 | Fowles et al. |
| 6,090,091 A | | 7/2000 | Fowles et al. |
| 6,090,092 A | | 7/2000 | Fowles et al. |
| 6,364,865 B1 | * | 4/2002 | Lavi et al. .................. 604/411 |

* cited by examiner

SPIKE FOR LIQUID TRANSFER DEVICE, LIQUID TRANSFER DEVICE INCLUDING SPIKE, AND METHOD OF TRANSFERRING LIQUIDS USING THE SAME

CROSS-REFERENCES TO RELATED APPLICATIONS

This is a continuation-in-part application of U.S. patent application Ser. No. 09/439,963, filed Nov. 12, 1999 now U.S. Pat. No. 6,478,771. U.S. patent application Ser. No. 09/439,963 claimed priority from U.S. Provisional Application No. 60/108,382, filed Nov. 13, 1998, and U.S. Provisional Application No. 60/131,644, filed Apr. 29, 1999.

BACKGROUND OF THE INVENTION

This invention relates generally to the field of liquid transfer. In particular, this invention relates to an improved spike or other needle, cannula, or penetrating member for facilitating the transfer of a liquid into a container such that little or no foaming occurs within the container, particularly when the liquid enters the container. This invention further relates to improved devices that utilize the spike. Such devices may include reconstitution, lyophilization, dilution, dissolution or drug transfer devices and injection or infusion combinations thereto as described and/or claimed, for example, in PCT Application No. PCT/US99/26751 (WO 00/29049), U.S. application Ser. No. 09/439,963, filed Nov. 12, 1999, U.S. Provisional Application No. 60/108,382, filed Nov. 13, 1998, U.S. Provisional Application No. 60/131,644, filed Apr. 29, 1999 and U.S. Provisional Application No. 60/234,118, filed Sep. 21, 2000, the disclosures of which are fully incorporated by reference herein.

Liquid transfer without foaming is very important, for example, in the field delivery of liquid medications for pharmaceutical and therapeutic use. Various devices have been developed for the percutaneous delivery of medications into living organisms. These devices include, for example, syringes, in which a liquid is delivered from a chamber using pressure asserted by a manual plunger through a needle inserted under the skin.

Of course, in the transfer of any other any liquids into and out of a container via a liquid jet or other liquid stream, even in fields unrelated to medicines, one may desire to minimize or prevent foaming. The present invention is directed to any conceivable transfer of liquid into a vial or other container that minimizes or eliminates such foaming during the transfer of the liquid.

In many fields, it is often necessary to lyophilize, reconstitute, dilute, dissolve, or mix a solid material, for example, a material in powdered form, or dilute or dissolve a liquid within a container. For purposes of the present invention, the terms reconstitution or reconstituting will be used to refer to any reconstitution, lyophilization, dilution, dissolution, mixing, or the like. This is accomplished by mixing the liquid or solid material with a suitable diluent, liquid, or solvent. Hereinafter, diluent will be used to refer to any diluent or other liquid or solvent used for reconstitution purposes in general. For example, such a diluent may be water or saline.

The reconstitution occurs when a diluent is transferred into a container having solid or liquid contents therein. The transfer of liquid into the container, especially under pressure, may cause considerable foaming. Where the ultimate solution is to be delivered to a mammal through a needle into the skin, such foaming must be avoided as the introduction of any gas into the tissue of mammal is not desirable and may be quite dangerous. Thus, it is desirable to have a simple, reliable system that facilitates preparation and safe reconstitution of a liquid or solid material within a container with minimal or no foaming. In addition, it may be desirable to provide a system that reconstitutes the liquid or solid material with minimal or no foaming while maintaining sterility throughout the process.

As indicated above, one element of such a system that must be taken into consideration is the need to prevent foaming. This may be accomplished by preventing the diluent fluid stream from directly hitting the liquid or solid material when it enters the container. Since some liquid or solid materials produce foam when a jet stream hits these materials, a fluid path that directs the liquid to directly impact the container contents is not desired. The present invention is directed to this shortcoming in the prior art.

An especially important area where minimization of foaming is desired is in the field of medicine. It is well known in the art that the storage life of certain injectable substances, for example, glucagon, which is used to dissolve blood clots, is increased when the substance is stored in a solid (e.g., powdered or lyophilized) or semisolid state. These powdered or lyophilized substances (i.e., drugs or compounds) are presently used for injection of materials that would otherwise be unstable. The resulting compound is typically stored in a glass container such as a vial, ampule, or cartridge, which is packaged under sterile conditions and enclosed within the container by securing a cap, such as a rubber stopper, membrane, or septum to the open end of the container.

As defined herein, powdered or lyophilized substances including drugs or other compounds will be designated generally as unreconstituted drugs.

In some cases, other drugs, although in a liquid state, must be diluted before use. As used herein, reconstitution with respect to medicines means to place a powdered or lyophilized drug or liquid drug into liquid form, as well as, to further dilute a liquid drug.

As indicated above, of particular interest at present are a wide range of medicaments produced by biochemical processes which are most stable when stored in a lyophilized form. Lyophilization is the rapid freezing of a material at a very low temperature followed by rapid dehydration by sublimation in a high vacuum. Lyophilization provides a product which is easily reconstitutable by the addition of a suitable solvent. Other medicaments may be provided as microparticles or nanoparticles which can be injected in a suspension formed by the addition of a suitable fluid thereto. Storage of medicaments in dry form can also be advantageous not only in terms of storage stability but also in terms of handling prior to use. Shipping costs and storage space can be reduced dramatically by employing a solid medicament form which is reconstituted, dissolved or diluted before use by, for example, the addition of water for injection. Moreover, sterility of the stored product may be better achieved is stored in such a solid form.

Prior to delivery, it is necessary to reconstitute the unreconstituted drugs. This is accomplished by mixing the solid compound with a suitable diluent, other liquid, or solvent. For example, diluents may be dextrose solution, saline solution, or water, as well as others. In the past, reconstitution of drugs typically involved the use of a syringe with a needle to withdraw a liquid such as a diluent from a separate vial by piercing a rubber septum into a separate the vial. The diluent is then injected through a rubber septum into a separate vial containing the unreconstituted, undiluted drug by piercing the rubber septum on the vial and injecting the diluent therein. The drug and diluent are then thoroughly mixed, typically by shaking the vial by hand. The desired amount of mixed solution is then withdrawn from the vial and injected into the patient.

Moreover, because the diluent and compound are in separate, sterilized containers, the manual withdrawal of diluent via a syringe and reinjection of the same into the container containing the unreconstituted drug may compromise sterility, health and safety due to the use of a syringe.

Additionally, many companies that manufacture a particular drug do not make the diluent and vice versa. Therefore, the unreconstituted drug and the diluent are sold separately. It is necessary for the doctor, pharmacist, nurse, or other medical person to mix the drug with diluent prior to use. Reconstituting the drug presents a number of problems.

Because of the use of such unreconstituted drugs, it is desirable to provide both professional and non-professional personnel with a drug delivery or mixing system to prepare and deliver the reconstituted drug. It is desirable to have a simple, reliable system that facilitates preparation and safe delivery of an accurate dosage of the reconstituted drug. In addition, it is desirable to provide a system that reconstitutes a drug while maintaining sterility throughout the process.

Of particular importance with drugs that require reconstitution is the need to prevent the diluent stream from directly hitting the powdered or lyophilized drug when it enters the drug vial. Since some drugs produce foam when the stream of diluent hits it, the introduction of the diluent directly upon the contents is not desired. The present invention is directed to this shortcoming in the prior art.

In the prior art, several reconstitution devices do exist which are presented herein as being of general background interest only. Related patents, U.S. Pat. Nos. 5,989,237 (Fowles et al.), 6,063,068 (Fowles et al.), 6,071,270 (Fowles et al.), 6,090,091 (Fowles), 6,109,750 (Fowles et al.) and 6,090,092 (Fowles et al.), provide a device for reconstituting a drug to be delivered to a patient. Here, the device has a first sleeve and a second sleeve where the first sleeve slides axially relative to the second sleeve. An end of the first sleeve is connected to a first container of diluent. The second sleeve, on the opposite side of the first container, is connected to a second container containing a drug. A piercing member, such as a double-ended cannula is provided within one of the first and second sleeves for accessing both the first and second containers and to establish fluid communication therebetween. The device is movable between an inactivated position and an activated position. When in the activated position, the containers are punctured by the piercing member, placing them in fluid communication so that the drug and diluent may be mixed.

U.S. Pat. No. 6,090,091 (Fowles et al.) provides a variation of the same invention, but further includes a means for sealing an end of the second sleeve member to the second container. The seal is an elastomeric disk-shaped septum having an axially extending resilient sleeve member that is dimensioned to fit about the piercing member to protect it from contamination. U.S. Pat. No. 6,019,750 (Fowles et al.) provides a septum for sealing an end of a medical container. The connector has an end to attach to a closure of a container. The closure has a target site and the connector has a piercing member therein for piercing the target site of the closure. The septum is a disk having a sheath extending axially from one surface of the disk and an annular ridge extending from the second surface of the disk. The annular ridge has a flared distal end, and the distal end is dimensioned to form a fluid tight seal with the target area of the closure.

U.S. Pat. No. 5,221,272 (Proni) provides a reusable quick fluid coupling assembly requiring a push for insertion, sealing, and locking, and a very slight squeeze for unlocking and removal to minimize the exposure of others to potentially dangerous structures capable of puncturing the human skin. The assembly also provides a universal system for a quick and secure fluid flow connection. The assembly includes a primary body having an channel coaxial to the longitudinal axis of the body, a non flexible central portion, a flexible retaining portion, and a portion integrally joining the nonflexible portion to the flexible portion. A diaphragm piercing, sharp-tipped, cylindrically shaped hollow needle is incorporated within and coaxial to the longitudinal axis of the primary body. The exterior surface of the needle is integrally attached to the surface of the non-flexible portion of the primary body and terminates within the flexible portion of the primary body. A removable conduit is disposed within the channel and has a diaphragm covered end that forms a fluid tight seal with the diaphragm piercing needle when the conduit is positioned along the length and locked in the channel.

None of these devices provides a piercing member that has multiple channels. Moreover, none of these devices is directed to minimize or eliminate foaming that may occur during the reconstitution process.

U.S. Pat. No. 5,454,786 (Harris) discloses a cartridge assembly for holding a lyophilized product that includes a glass drug vial that contains the lyophilized product and a closure cap having a rubber seal. The assembly includes a syringe having a needle. Reconstitution of the lyophilized drug is accomplished without foaming by use of an obliquely angled connector between the syringe and the vial which causes diluent to indirectly impinge on the drug. Here, however, the needle, the syringe and the stream of diluent exiting the needle are all coaxial creating a somewhat cumbersome device due to its length.

Without further elaboration, the foregoing will so fully illustrate the present invention that others may, by applying current or future knowledge, readily adopt the same for use under various conditions of service.

SUMMARY OF THE INVENTION

The present invention is directed to a spike for facilitating the introduction of liquid under pressure into a container containing a substance. The spike includes an elongate spike shaft having a spike side wall, a longitudinal axis, a distal end and a proximally located end portion, The distal end has a sharp, pointed tip. The spike also has an introduction channel within the spike shaft for receiving liquid into the container. A portion of the introduction channel is angled to cause liquid to travel out of the introduction channel in a direction non-parallel to the longitudinal axis of the spike shaft.

In one preferred embodiment of the present invention, a spike is provided for facilitating the introduction of liquid under pressure into a container containing a substance. The spike includes an elongate spike shaft having a spike side wall, a longitudinal axis, a distal end and a proximally located end portion. The distal end has a sharp, pointed tip. An introduction channel is located within the spike shaft for receiving liquid into the container, where a portion of the introduction channel is angled to cause liquid to travel out of the introduction channel in a direction non-parallel to the longitudinal axis of the spike shaft. The spike may include an extraction channel within the spike shaft for removing liquid from the container, where the extraction channel extends through the elongate spike shaft towards the proximally located end portion. Preferably, the portion of the introduction channel is perpendicular to the longitudinal axis. The introduction channel may include a main leg extending from the proximally located end portion towards the distal end, at or substantially parallel to the longitudinal axis, and an exit leg extending from the main leg to a diluent outlet opening in the spike side wall. The exit leg may extend from the main leg perpendicular to the longitudinal axis.

The extraction channel may have an inlet opening in the spike shaft for receiving liquid from the container and the introduction channel may have a diluent outlet opening in the spike shaft. The inlet opening is preferably closer to the proximally located end portion than the diluent outlet opening.

A device for reconstituting a substance in a first liquid to provide a resulting liquid comprising the first liquid and the substance subsequent to being reconstituted is also provided. Here, the spike is provided as described above. The device further includes a chamber containing the first liquid under pressure and a container containing the substance. The container has at least one container side wall and a capped end, and the capped end has a cap having a pierceable portion. The spike extends through the pierceable portion into the container.

A hand-held drug reconstitution and injection device is also provided which includes the drug reconstitution spike as described above, a diluent vial containing a diluent and having an elongate diluent vial spike extending through a diluent vial cap on the diluent vial. The diluent vial spike includes a distal end located inside the diluent vial, a diluent vial spike side wall, and a proximally located lower portion located outside the diluent vial. The diluent vial spike also includes a diluent vial spike air inlet conduit extending between an air inlet conduit opening in the proximally located lower portion and a diluent vial spike side wall opening adjacent the distal end. The diluent vial spike also includes a diluent exit conduit extending between an entrance opening on the diluent vial spike side wall adjacent the distal end and an exit opening on the proximally located lower portion of the diluent vial spike. The device also includes a drug vial containing a substance to be reconstituted, where the drug vial has at least one drug vial side wall and a capped end having a cap having a pierceable membrane. The drug vial has a drug vial spike extending through the drug vial cap on the drug vial as described above. An air conduit extends between an air pressurizer and the air inlet conduit opening. A diluent conduit extends between the exit opening and the diluent inlet opening for transfer of the diluent through the diluent conduit from the diluent vial to the drug vial. A reconstituted drug conduit extends between the extraction channel outlet opening and a needle having an orifice therein for injection into a patient. The reconstituted drug conduit may include an air separator to separate air from the reconstituted drug prior to injection. The air separator may be a hydrophilic membrane. The air pressurizer may be a cylinder and plunger.

Finally, a spike for the introduction of liquid under pressure into a container and for the withdrawing of liquid from the container is provided that includes an elongate spike shaft having a spike side wall, a longitudinal axis, a distal end and a proximally located end portion. The distal end has a sharp, pointed tip. The spike includes an introduction channel within the spike shaft for receiving liquid into the container and an extraction channel within the spike shaft for removing liquid from the container. The extraction channel has an inlet opening on the spike shaft inside the container for receiving liquid from the container and the introduction channel has a diluent outlet opening on the spike shaft for delivering liquid into the container. The inlet opening is closer to the proximally located end portion than the diluent outlet opening.

Methods of utilizing the above mentioned embodiments are also provided.

DETAILED DESCRIPTION OF THE PREFERRED EMBODIMENT

This invention relates to an improved device for facilitating the transfer of a liquid into a container having a solid or liquid therein such that little or no foaming occurs. While the present invention is not necessarily intended to be limited for use only with medicines that require reconstitution, the particular preferred embodiment described herein is directed generally to a drug delivery system and method. It is understood that the present invention may be equally applicable for any transfer of liquid into and out of a container where it is desired that foaming be minimized or eliminated.

In this preferred embodiment of a drug delivery system, the system provides generally for the delivery of a drug in solution, under pressure, and more particularly to the injection of drugs that require reconstitution. The drug delivery system includes a reconstitution system, a pressurization system to facilitate drug delivery, a transfer system, and an injector system. Different embodiments of the drug delivery system may use only the reconstitution system alone or the reconstitution system with one or more of the systems described. Other embodiments can employ a combination of these systems, depending on the requirements of the different applications.

The preferred embodiment of the present invention described here is specifically directed to the need to prevent the diluent fluid stream from directly hitting the unreconstituted drug when it enters the drug vial. Since some drugs produce foam when the stream of diluent impacts the drug, directing the fluid stream of diluent so that it directly impacts the drug should be avoided. This is not a desired result in drug delivery as the solution must be free of any gas or air pockets prior to the delivery. The solution here is to direct the fluid pathway of the diluent as it travels into the drug container in such a way that it does not directly impact the drug. This is accomplished by directing the diluent fluid pathway to initially impact the side of the vial. By having the axis of the incoming fluid enter at an angle relative to and preferably perpendicular to the vial wall, the angled fluid stream inhibits the foaming action of the drug.

Figure 1:
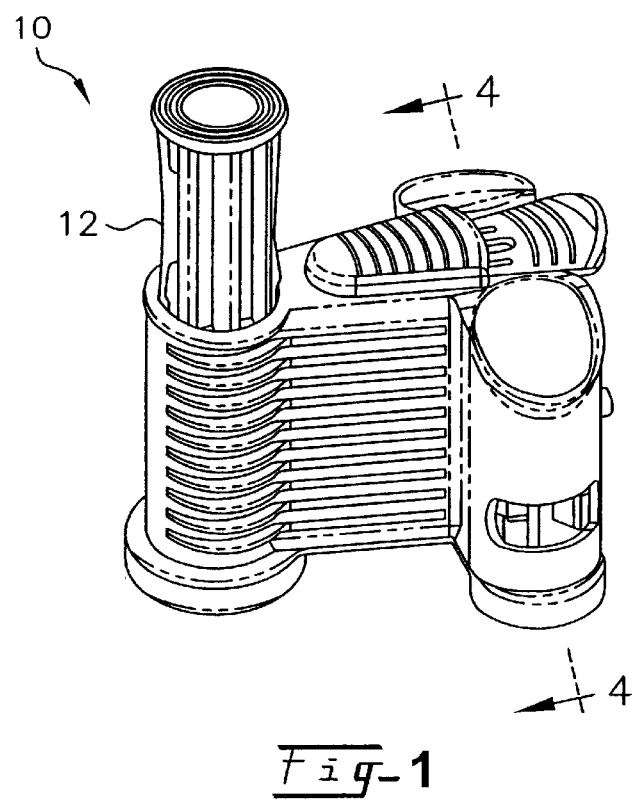
FIG. 1 is an isometric view of the front side of an example of a hand-held drug reconstitution device that utilizes the drug spike in accordance with one preferred embodiment of the present invention, wherein a plunger for transferring diluent from a diluent vial to a drug vial and for pressurizing the device is in an extended position.
Figure 2:
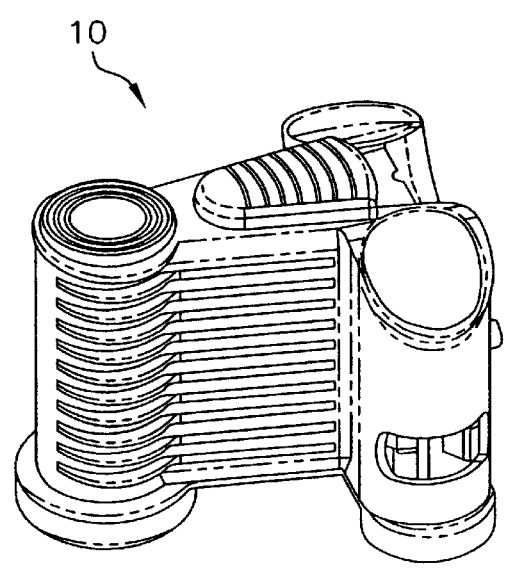
FIG. 2 is an isometric view of the rear side of the example of a hand-held drug reconstitution device of FIG. 1 wherein the plunger is in a fully inserted position.
Figure 5:
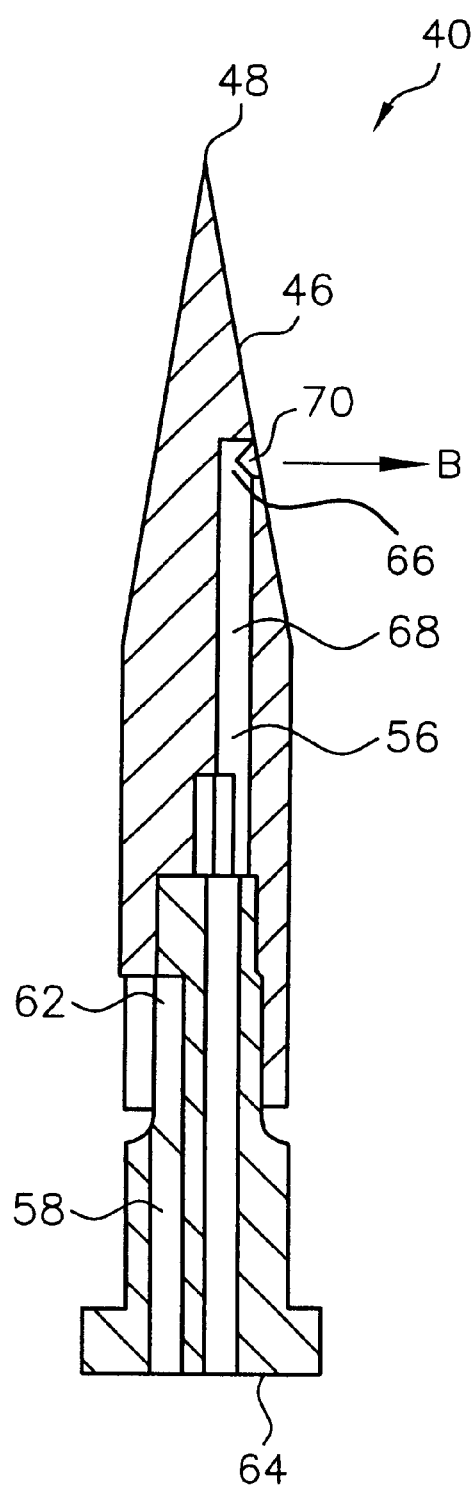
FIG. 5 is an enlarged cross-sectional view of the drug device spike of the present invention as used on the drug reconstitution device of FIG. 1.

Referring now to the various figures of the drawing wherein like reference numbers refer to like parts throughout the several views, there is shown in FIGS. 1 and 2 one preferred embodiment of a drug reconstitution device 10 for use with one preferred embodiment of a drug spike 20 as depicted in FIG. 5 of the present invention. FIG. 1 depicts the drug reconstitution device 10 with its plunger 12 depicted in an extended position while FIG. 2 depicts the drug reconstitution device 20 with its plunger 12 depicted in a fully inserted position, as will be explained below.

Figure 3:
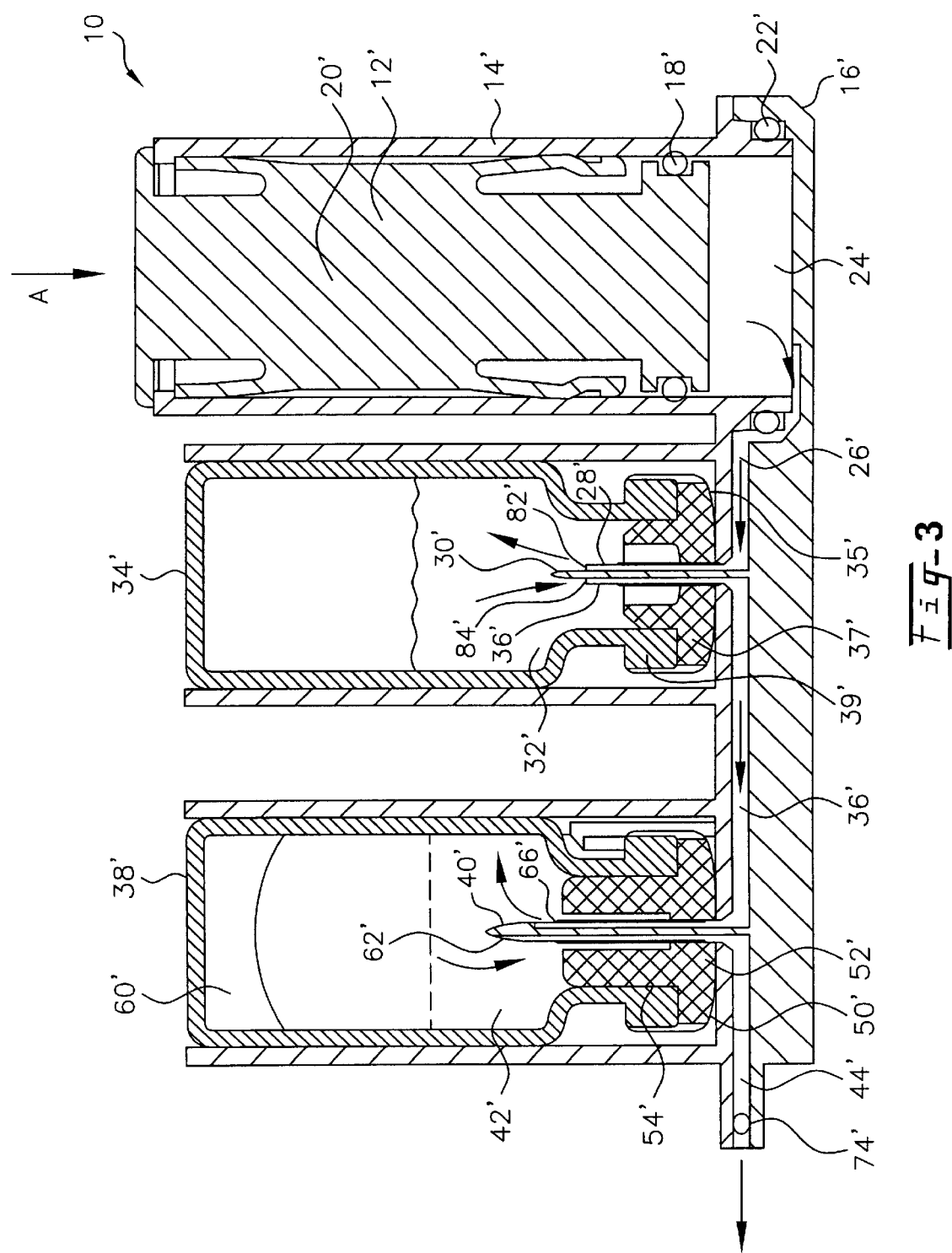
FIG. 3 is a simplified schematic of the operation of a hand held reconstitution device that uses the drug device spike in accordance with the present invention depicting the air and liquid pathways within the device.

FIG. 3 depicts, in schematic form, the operation of the drug reconstitution device 10 and drug spike 40 of the present invention. For the sake of convenience, an apostrophe will be added to the reference numbers of FIG. 3 which represent the like parts of the actual embodiment of the remaining figures herein. For example, drug reconstitution device 10 of FIG. 1 will be referenced as drug reconstitution device 10' in the schematic of FIG. 3. Reference numbers with and without apostrophes will be used interchangeably in this manner for like parts throughout the several views. In FIG. 3, there is shown as part of the drug reconstitution device 10' a main housing 14' in combination with a lower housing 16'. A standard diluent vial 34' (typically a glass vial that includes a puncturable rubber stopper held in place by an aluminum foil shell) is installed within the device 10' wherein the foil shell 35' is first removed and the diluent spike 30' pierces through rubber layers 37' and through the neck 39' of the diluent vial 34'. Likewise, a standard drug vial 38' containing unreconstituted drug 60' is installed within the device 10' such that drug spike 40' pierces through an outer foil shell 50' and rubber layers 52' and through neck 54' of the drug vial 38'.

In FIG. 3, plunger 12' is depicted in a fully inserted position as was seen in FIG. 2. Plunger 12' is capable of moving axially downwardly along the line of travel depicted as A in FIG. 3 from the extended position (as shown in FIG. 1). A seal, such as O-ring seal 18' creates an airtight seal between the piston section 20' of plunger 12'. Another O-ring seal 22' makes an airtight seal between the lower housing 16' and the main housing 14'.

As plunger 12' moves from the extended position (of FIG. 1) to the fully inserted position as shown here in FIGS. 2 and 3, air within piston chamber 24' is forced downwardly as the piston chamber 24' is reduced in volume and through first (air) conduit 26' and through an air inlet conduit opening 80', through air inlet channel 28', and out a side wall opening 82' in diluent spike 30'. The air passes through the diluent 32' up to the top of diluent vial 34' and increases the pressure within the diluent vial 34' such that diluent 32' is forced through an entrance opening 84', through second (diluent) conduit 36', out exit opening 86' and ultimately into drug vial 38' through the drug device spike 40' of the present invention.

Of course, the pressurization system as shown in FIG. 3 is not necessary as any means to create a pressurized volume of a diluent would suffice.

It is noted that the unreconstituted drug 60' may exist in a consolidated form at the upper end of the drug vial 38'. Swirling of the diluent when it reaches the drug vial will ensure proper mixing. The diluent 32' reconstitutes the drug 60' and the reconstituted drug 42' is pressurized for exiting via third (reconstituted drug) conduit 44'.

The pressurizing means as depicted herein is the plunger 12' and piston 20' within the piston chamber. Other pressurizing systems or air sources as known in the art may be used, for example, a compressed air supply, a chemical gas generator, a collapsible volume supply, a bellow canister, or a standard syringe or cylinder. The air source supplies the driving force to the diluent volume which moves the diluent into the drug vial. Once reconstituted, the reconstituted drug is transferred via an air separator, such as a hydrophilic membrane 74' as known in the art to an injection needle to minimize or preferably prevent the entry of air into the user's tissue. The hydrophilic membrane 74' is disposed in the drug path to the user's tissue. Once wetted, the hydrophilic membrane 74' allows liquid drug to proceed into the user's tissue and stops the passage of air into the users' tissue. In order to ensure the effectiveness of the membrane, the hydrophilic membrane must become wetted. A hydrophobic membrane may also be used to allow air to pass, but to stop liquids (not shown).

Once the drug 60 is diluted by the diluent 32' such that it is now a reconstituted drug 42', the reconstituted drug 42' is ready for injection. In the preferred device, the device 10' includes an injection assembly containing a needle assembly. The needle assembly is in liquid communication with the reconstituted drug fluid pathway as it exits the diluent vial under pressure. In use, the injection assembly is activated to cause the needle assembly to move from a recessed position within the device of housing to an extended position. As the device housing is pressed against the skin of the person to be injected, the needle pierces the user's skin and enables the reconstituted drug to travel via the needle into the user's skin.

Figure 4:
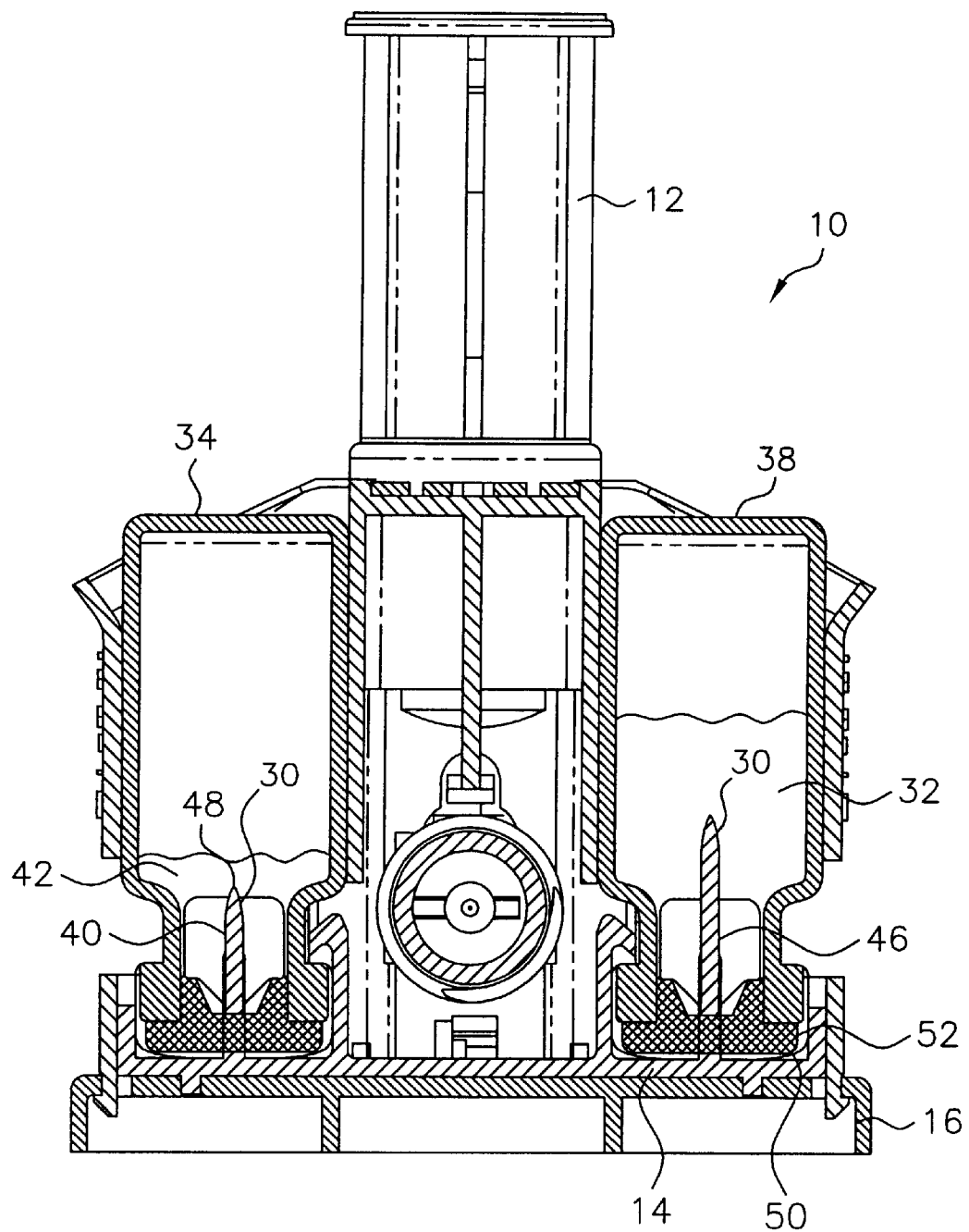
FIG. 4 is a cross-sectional view of the drug reconstitution device as shown in FIG. 1, taken substantially along line 4—4 of FIG. 1.

FIG. 4 depicts a cross sectional view of the drug reconstitution device 10 and depicts a drug spike 40 in accordance with the present invention, a drug vial 38, a diluent spike 30 and a diluent vial 34. This drug reconstitution device operates in accordance with the schematic of FIG. 3. The diluent vial 34 is inserted upside down so that the head and neck of the diluent vial 34 are received into the diluent spike 30. The drug vial 38 is inserted upside down so that the drug spike 40 of the present invention is received into the head and neck of the drug vial 38. The drug spike 40 directs diluent 32 into the drug vial without the solution foaming and to more efficiently extract a reconstituted drug 42 without air pockets from the drug vial 38 for delivery to the user.

As can be seen in FIG. 5 (and FIGS. 3 and 4), the drug device spike 40 generally includes a spike 46 having a sharp pointed tip 48 adapted to pierce the rubber layer or layers (e.g. a membrane or septum) 52 of the drug vial 38. The spike 40 has a shape and size such that it may be received into the neck 54 of the drug vial 38 along with any other items in the drug vial neck 54 such as a portion of rubber layer 52. In addition, the spike 40 has a pair of channels, an introduction channel 56 and an extraction channel 58. The introduction channel 56 is preferably L-shaped, as will be explained in more detail below, and is designed to receive incoming diluent, from an outside source, e.g., from the diluent vial 34, into the drug vial 38. The introduction channel 56 accepts pressurized diluent 32 entering the drug vial 38 through a diluent inlet opening 73 at the proximal end of the spike and directs the diluent outwardly to the side of the drug vial 38 through a diluent outlet opening 66 in the spike as shown by arrow B (rather than along the longitudinal axis of the spike), thereby preventing direct impact of the diluent fluid stream against the drug 60 in the drug vial 38, and thereby substantially reducing the potential for foaming. The extraction channel 58 is elongated and serves to extract drug solution from the drug vial 38 through an extraction channel outlet opening 75 for subsequent delivery. The extraction channel inlet opening 62 is preferably closer to the proximal end 64 of the spike 46 opposite the distal end of the spike, tip 48, than the diluent outlet opening 66 of the introduction channel 56 to enable a larger volume of the reconstituted drug solution 42 to be extracted from the drug vial 38 so that a minimum of reconstituted drug 42 is left in the drug vial 38 and a more accurate delivery of drug is possible.

The L-shaped introduction channel 56 is preferably constructed of a main channel 68 and an exit leg 70 that is at a substantial angle to the main channel 68, and preferably perpendicular thereto. As indicated above, the angle of the exit leg 70 now causes the incoming diluent 32 stream to strike the side wall 72 of drug vial 38 so that the stream of diluent 32 does not directly impact the drug 60 in the drug vial 38. Prior to reconstitution, the drug is typically packed at the end of the drug vial 38 opposite the neck 38. In the past, diluent introduced into the drug vial was directed in such a way that the diluent stream traveled along the vertical axis of the vial and struck the compacted drug against the end of the vial. Such a system resulted in significant foaming of the reconstituted solution. As a result, the solution containing the foam had to be left alone for a significant period of time in order to allow the foam to dissipate or the solution had to be abandoned altogether. This resulted in a waste of valuable and expensive drug, as well as time and effort on the part of the user or health care provider. In addition, if a new solution of reconstituted drug was required to be created, the time in getting the ultimate solution to the patient is delayed which may result in a loss of patient compliance with a prescribed delivery schedule.

As noted above, this L-shaped feature in the introduction channel 56 minimizes or eliminates foaming by directing the incoming diluent fluid stream to the side of the drug vial 38 thereby substantially preventing direct contact between the incoming diluent 32 and dry drug 60. The diluent 32 then moves along the side wall 72 of the drug vial 38 at a substantially reduced speed before making contact and mixing with the drug 60.

In this DRIS™ system, each spike includes two paths, a first for incoming fluid and a second for outgoing fluid. Preferably the spike is injection molded from a plastic. Most spikes, however, only include a single path. Relatively bigger spikes have been made, for example, for the nutrition market. Here, two spikes are included, but the second spike is to allow air to get into a rigid container while emptying the fluid therefrom.

The existence of two spikes does have an effect on the penetrating force of the spike. The penetrating force is connected to several parameters—the diameter of the spike, the tip quality, the surface quality, and the coefficient of friction between the septum and the spike. In a typical application, e.g. in penetrating the bromobuytl rubber septum of a standard 4 ml vial, the penetration force of the spike of the present invention is reduced to about 1.6 kg from over 3 kg for other spikes.

It must be appreciated that the present invention may be used to deliver a number of drugs. The term "drug" as used herein includes, but is not limited to peptides or proteins (and mimetic thereof), antigens, vaccines, hormones, analgesics, anti-migraine agents, anti-coagulant agents, medications directed to the treatment of diseases and conditions of the central nervous system, narcotic antagonists, immunosuppressants, agents used in the treatment of AIDS, chelating agents, anti-anginal agents, chemotherapy agents, sedatives, anti-neoplastics, prostaglandins, antidiuretic agents and DNA or DNA/RNA molecules to support gene therapy.

Typical drugs include peptides or proteins (and mimetic thereof) such as insulin, calcitonin, calcitonin gene regulating protein, atrial natriuretic protein, colony stimulating factor, betaseron, erythropoietin (EPO), interferons such as α, β, or γ interferon, somatropin, somatotropin, somastostatin, insulin-like growth factor, (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2 and analogues or antagonists thereof, such as IL-1ra; analgesics such as fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogues thereof; anti-migraine agents such as sumatriptan, ergot alkaloids, and analogues thereof; anti-coagulant agents such as heparin, hirudin, and analogues thereof, anti-emetic agents such as scopolamine, ondansetron, domperidone, metoclopramide, and analogues thereof; cardiovascular agents, anti-hypertensive agents, and vasodilators such as diltiazem, clonidine, nifedipine, verapamil, isosorbide-5-monotitrate, organic nitrates, agents used in treatment of heart disorders, and analogues thereof; sedatives such as benzodiazepines, phenothiazines, and analogues thereof; chelating agents such as defroxanune, and analogues thereof; antidiuretic agents such as desmopressin, vasopressin, and analogues thereof, anti-anginal agents such as fluorouracil, bleomycin and analogues thereof; anti-neoplastics such as fluorouracil, bleomycin, and analogues thereof; prostaglandins and analogues thereof; and chemotherapy agents such as vincristine, and analogues thereof, treatments for attention deficit disorder, methylphenidate, fluvoxamine, bisoprolol, tacrolimus, sacrolimus, and cyclosporin.

While the invention has been described in detail and with reference to specific embodiments thereof, it will be apparent to one skilled in the art that various changes and modifications can be made therein without departing from the spirit and scope thereof.

What is claimed is:

1. A spike for facilitating the introduction of liquid under pressure into a container containing a substance, said spike comprising:

(a) an elongate spike shaft having a spike side wall, a longitudinal axis, a distal end and a proximally located end portion, said distal end having a sharp, pointed tip;

(b) an introduction channel within said spike shaft for receiving liquid into the container, a portion of said introduction channel angled to cause liquid to travel out of the introduction channel in a direction non-parallel to said longitudinal axis of said spike shaft; and (c) an extraction channel within said spike shaft for removing liquid from said container, said extraction channel extending through said elongate spike shaft towards said proximally located end portion, said extraction channel not coaxial with said introduction channel said extraction channel having an inlet opening in said spike shaft for receiving liquid from said container and said introduction channel having a diluent outlet opening in said spike shaft, wherein said inlet opening is closer to said proximally located end portion than said diluent outlet opening.

2. The spike of claim 1, wherein said portion of said introduction channel is perpendicular to said longitudinal axis.

3. The spike of claim 1, wherein said introduction channel has a main leg extending from said proximally located end portion towards said distal end, at or substantially parallel to said longitudinal axis, and an exit leg extending from said main leg to a diluent outlet opening in said spike side wall.

4. The spike of claim 3, wherein said exit leg extends from said main leg perpendicular to said longitudinal axis.

5. A device for reconstituting a substance in a first liquid to provide a resulting liquid comprising the first liquid and the substance subsequent to being reconstituted, the device, comprising:
   (a) a chamber containing the first liquid under pressure;
   (b) a container containing the substance, said container having at least one container side wall and a capped end, said capped end having a cap having a pierceable portion;
   (c) a spike extending through said pierceable portion into said container, said spike comprising:
      (i) an elongate spike shaft having a spike side wall, a longitudinal axis, a distal end and a proximally located end portion, said distal end having a sharp, pointed tip; and
      (ii) an introduction channel within said spike shaft for receiving the first liquid into said container, a portion of said introduction channel angled to cause liquid to travel out of the introduction channel in a direction non-parallel to said longitudinal axis of said spike shaft; and
   (d) an extraction channel within said spike shaft for removing the resulting liquid from said container, said extraction channel extending through said elongate spike shaft towards said proximally located end portion, said extraction channel not coaxial with said introduction channel, said extraction channel having an inlet opening in said shaft and said introduction channel having a diluent outlet opening in said shaft and wherein said inlet opening is closer to said proximally located end portion than said diluent outlet opening.

6. The device of claim 5, wherein said portion of said introduction channel is perpendicular to said longitudinal axis.

7. The device of claim 5, wherein said introduction channel has a main leg extending from said proximally located end portion towards said distal end, at or substantially parallel to said longitudinal axis, and an exit leg extending from said main leg to a diluent outlet opening in said spike side wall.

8. The device of claim 7, wherein said exit leg is perpendicular to said longitudinal axis.

9. The device of claim 5, wherein said pierceable portion is a rubber membrane.

10. A hand-held drug reconstitution and injection device, comprising:
    (a) a diluent vial containing a diluent and having an elongate diluent vial spike extending through a diluent vial cap on said diluent vial, said diluent vial spike comprising:
       (i) a distal end located inside said diluent vial, a diluent vial spike side wall, and a proximally located lower portion located outside said diluent vial;
       (ii) a diluent vial spike air inlet conduit extending between an air inlet conduit opening in said proximally located lower portion and a diluent vial spike side wall opening adjacent said distal end; and
       (iii) a diluent exit conduit extending between an entrance opening on said diluent vial spike side wall adjacent said distal end and an exit opening on said proximally located lower portion of said diluent vial spike;
    (b) a drug vial containing a substance to be reconstituted, said drug vial having at least one drug vial side wall and a capped end, said capped end having a cap having a pierceable membrane, said drug vial having a drug vial spike extending through said drug vial cap on said drug vial, said drug vial spike comprising:
       (i) an elongate spike shaft having a spike side wall, a longitudinal axis, a distal end located inside said drug vial, and a proximally located end portion located outside said drug vial, said distal end having a sharp, pointed tip;
       (ii) an introduction channel within said spike shaft for receiving the diluent into said drug vial, a portion of said introduction channel angled to cause the diluent to travel out of the introduction channel in a direction non-parallel to said longitudinal axis of said spike shaft; said introduction channel having a diluent inlet opening on said proximally located end portion and a diluent outlet opening in said spike side wall adjacent said distal end; and
       (iii) an extraction channel within said spike shaft for removing a reconstituted drug from said drug vial, said extraction channel extending from an extraction channel inlet opening in said spike side wall adjacent said distal end to an extraction channel outlet opening in the proximally located end portion;
    (c) an air conduit extending between an air pressurizer and said air inlet conduit opening;
    (d) a diluent conduit extending between said exit opening and said diluent inlet opening, for transfer of said diluent through said diluent conduit from said diluent vial to said drug vial; and
    (e) a reconstituted drug conduit extending between said extraction channel outlet opening and a needle having an orifice therein for injection into a patient.

11. The spike of claim 10, wherein said portion of said introduction channel is perpendicular to said longitudinal axis.

12. The spike of claim 10, wherein said introduction channel has a main leg extending from said diluent inlet opening towards said distal end, at or substantially parallel to said longitudinal axis, and an exit leg extending from said main leg to said diluent outlet opening in said spike side wall.

13. The device of claim 10, wherein said exit leg is perpendicular to said longitudinal axis.

14. The device of claim 10, wherein said extraction channel inlet opening is closer to said proximally located end portion than said diluent outlet opening.

15. The device of claim 10, wherein said reconstituted drug conduit includes an air separator to separate air from the reconstituted drug prior to injection.

16. The device of claim 15, wherein the air separator is a hydrophilic membrane.

17. The device of claim 10, wherein the air pressurizer is a cylinder and plunger.

18. A spike for the introduction of liquid under pressure into a container and for the withdrawing of liquid from the container, said spike comprising:
    (a) an elongate spike shaft having a spike side wall, a longitudinal axis, a distal end and a proximally located end portion, said distal end having a sharp, pointed tip;

(b) an introduction channel within said spike shaft for receiving liquid into said container, said introduction channel including a main leg extending from said proximally located end portion towards said distal end, at or substantially parallel to said longitudinal axis, and an exit leg extending from said main leg to a diluent outlet opening in said spike side wall;

(c) an extraction channel within said spike shaft for removing liquid from said container, and (d) said extraction channel having an inlet opening on said spike shaft inside the container for receiving liquid from the container and said introduction channel having a diluent outlet opening on said spike shaft for delivering liquid into said container, wherein said inlet opening is closer to said proximally located end portion than said diluent outlet opening.

19. A method for introducing liquid under pressure into a container containing a substance, comprising the steps of:

(a) providing an elongate spike shaft having a spike side wall, a longitudinal axis, a distal end and a proximally located end portion, said distal end having a sharp, pointed tip;

(b) providing an introduction channel within said spike shaft, a portion of said introduction channel angled to cause the liquid to travel out of the introduction channel in a direction non-parallel to said longitudinal axis of said spike shaft;

(c) providing the liquid under pressure into said container through said introduction channel such that the liquid travels out of said spike shaft in a direction non-parallel to said longitudinal axis of said spike shaft; and (d) providing an extraction channel within said spike shaft, said extraction channel extending through said elongate spike shaft towards said proximally located end portion and including the step of removing liquid from said container through said extraction channel.

20. The method of claim 19, wherein the step of providing said introduction channel includes providing said portion of said introduction channel perpendicular to said longitudinal axis.

21. The method of claim 19, wherein said step of providing said introduction channel includes providing a main leg extending from said proximally located end portion towards said distal end, at or substantially parallel to said longitudinal axis, and providing an exit leg extending from said main leg to a diluent outlet opening in said spike side wall.

22. The method of claim 21, wherein said step including providing said exit leg includes providing said exit leg extending from said main leg perpendicular to said longitudinal axis.

23. The method of claim 19, wherein said step of providing said extraction channel includes providing an inlet opening in said spike shaft for receiving liquid from said container and wherein said step of providing said introduction channel includes providing a diluent outlet opening in said spike shaft, wherein said inlet opening is closer to said proximally located end portion than said diluent outlet opening.

24. A method for reconstituting a substance in a first liquid to provide a resulting liquid comprising the first liquid and the substance subsequent to being reconstituted, said method comprising:

(a) providing a chamber containing the first liquid;

(b) providing a container containing the substance, said container having at least one container side wall and a capped end, said capped end having a cap having a pierceable portion; and (c) providing a spike comprising:
(i) an elongate spike shaft having a spike side wall, a longitudinal axis, a distal end and a proximally located end portion, said distal end having a sharp, pointed tip; and
(ii) an introduction channel within said spike shaft for receiving the first liquid into said container, a portion of said introduction channel angled to cause liquid to travel out of the introduction channel in a direction non-parallel to said longitudinal axis of said spike shaft;

(d) providing a diluent conduit extending between chamber and said introduction channel of said spike, for transfer of said diluent through said diluent conduit from said chamber to said container;

(e) piercing said spike through said pierceable portion into said container; and (f) pressurizing said first liquid in said chamber to cause said first liquid to flow from said chamber, through said diluent conduit and into said container through said introduction channel.

25. The method of claim 24, the step of providing an extraction channel within said spike shaft for removing the resulting liquid from said container, said extraction channel extending through said elongate spike shaft towards said proximally located end portion.

26. The method of claim 24, wherein the step of providing the introduction channel includes providing said portion of said introduction channel perpendicular to said longitudinal axis.

27. The method of claim 24, wherein the step of providing said introduction channel includes providing a main leg extending from said proximally located end portion towards said distal end, at or substantially parallel to said longitudinal axis, and providing an exit leg extending from said main leg to a diluent outlet opening in said spike side wall.

28. The method of claim 27, wherein said step including providing said exit leg includes providing said exit leg perpendicular to said longitudinal axis.

29. The method of claim 25, wherein said step of providing said extraction channel includes providing an inlet opening in said shaft and said step of providing said introduction channel includes providing a diluent outlet opening in said shaft, wherein said inlet opening is closer to said proximally located end portion than said diluent outlet opening.

30. The method of claim 24, wherein said step including providing said pierceable portion includes providing a rubber membrane.

31. A method for reconstituting a drug, comprising:

(a) providing a diluent vial spike comprising:
(i) a distal end, a diluent vial spike side wall, and a proximally located lower portion;
(ii) a diluent vial spike air inlet conduit extending between an air inlet conduit opening in said proximally located lower portion and a diluent vial spike side wall opening adjacent said distal end; and
(iii) a diluent exit conduit extending between an entrance opening on said diluent vial spike side wall adjacent said distal end and an exit opening on said proximally located lower portion of said diluent vial spike;

(b) providing a diluent vial having a diluent vial cap and containing a diluent;

(c) extending said distal end of said elongate diluent vial spike through said diluent vial cap;

(d) providing a drug vial containing a substance to be reconstituted, said drug vial having at least one drug vial side wall and a capped end, said capped end having a cap having a pierceable membrane;

(e) providing a drug vial spike comprising:
   (i) an elongate spike shaft having a spike side wall, a longitudinal axis, a distal end, and a proximally located end portion, said distal end having a sharp, pointed tip;
   (ii) an introduction channel within said spike shaft for receiving the diluent into said drug vial, a portion of said introduction channel angled to cause the diluent to travel out of the introduction channel in a direction non-parallel to said longitudinal axis of said spike shaft; said introduction channel having a diluent inlet opening on said proximally located end portion and a diluent outlet opening in said spike side wall adjacent said distal end; and
   (iii) an extraction channel within said spike shaft for removing a reconstituted drug from said drug vial, said extraction channel extending from an extraction channel inlet opening in said spike side wall adjacent said distal end to an extraction channel outlet opening in the proximally located end portion;

(f) piercing said drug vial spike through said drug vial cap such that said distal end of said drug vial spike is located inside said drug vial and said proximally located end portion is located outside said drug vial;

(g) providing an air conduit extending between an air pressurizer and said air inlet conduit opening;

(h) providing a diluent conduit extending between said exit opening and said diluent inlet opening, for transfer of said diluent through said diluent conduit from said diluent vial to said drug vial;

(i) providing a reconstituted drug conduit extending between said extraction channel outlet opening and a needle having an orifice therein for injection into a patient; and (j) pressurizing said diluent vial using said air pressurizer to cause air to flow through said air conduit to said air inlet conduit opening, to cause diluent to flow out of said diluent exit conduit, through said diluent conduit, and through said introduction channel to mix with said substance and to cause said reconstituted drug to flow through said extraction channel and through said orifice in said needle.

32. The method of claim 31, wherein said step including providing said introduction channel is includes providing said portion of said introduction channel perpendicular to said longitudinal axis.

33. The method of claim 31, wherein said step of providing said introduction channel includes providing a main leg extending from said diluent inlet opening towards said distal end, at or substantially parallel to said longitudinal axis, and providing an exit leg extending from said main leg to said diluent outlet opening in said spike side wall.

34. The method of claim 31, wherein said step including providing said introduction channel includes providing said exit leg perpendicular to said longitudinal axis.

35. The method of claim 31, wherein the step of providing said extraction channel includes providing said extraction channel inlet opening closer to said proximally located end portion than said diluent outlet opening.

36. The method of claim 31, wherein said step including providing said reconstituted drug conduit includes providing an air separator to separate air from the reconstituted drug prior to injection.

37. The method claim 36, wherein step of providing the air separator includes providing a hydrophilic membrane.

38. The method of claim 31, wherein the step including providing an air pressurizer includes providing a cylinder and plunger.

39. A method for introducing liquid under pressure into a container and for withdrawing liquid from the container, said method comprising:

(a) providing an elongate spike shaft having a spike side wall, a longitudinal axis, a distal end and a proximally located end portion, said distal end having a sharp, pointed tip;

(b) providing an introduction channel within said spike shaft for receiving liquid into said container, said introduction channel having a diluent outlet opening on said spike shaft for delivering liquid into said container, a portion of said introduction channel being non-parallel to said longitudinal axis of said spike shaft;

(c) providing an extraction channel within said spike shaft for removing liquid from said container, said extraction channel having an inlet opening on said spike shaft inside the container for receiving liquid from the container, wherein said inlet opening is closer to said proximally located end portion than said diluent outlet opening;

(d) receiving liquid into said container through said introduction channel; and (e) withdrawing liquid from said container through said extraction channel.

* * * * *